United States Patent [19]

See

[11] Patent Number: 5,718,917

[45] Date of Patent: Feb. 17, 1998

[54] PGE-1 CONTAINING LYOPHILIZED LIPOSOMES FOR USE IN THE TREATMENT OF ERECTILE DYSFUNCTION

[75] Inventor: Jackie R. See, Las Vegas, Nev.

[73] Assignee: Harvard Scientific Corporation, Reno, Nev.

[21] Appl. No.: 573,408

[22] Filed: Dec. 15, 1995

[51] Int. Cl.$^6$ ..................................... A61K 9/127
[52] U.S. Cl. ................................. 424/450; 514/559
[58] Field of Search ............... 424/450; 514/559, 514/929

[56] References Cited

U.S. PATENT DOCUMENTS

| | | |
|---|---|---|
| 246,697 | 9/1881 | Wadleigh . |
| 251,355 | 12/1881 | Gibbs . |
| 3,993,754 | 11/1976 | Rahman et al. ............... 424/177 |
| 4,114,179 | 9/1978 | Ilieve ............................. 358/34 |
| 4,145,410 | 3/1979 | Sears ............................. 424/19 |
| 4,235,871 | 11/1980 | Papahadjopoulos ............ 424/19 |
| 4,474,773 | 10/1984 | Shinitzky et al. ............. 424/199 |
| 4,478,822 | 10/1984 | Haslam et al. ................ 424/78 |
| 4,493,847 | 1/1985 | Mizushima et al. .......... 424/317 |
| 4,522,803 | 6/1985 | Lenk et al. .................... 424/1.1 |
| 4,533,254 | 8/1985 | Cook et al. ................... 366/176 |
| 4,588,578 | 5/1986 | Fountain et al. ............. 424/1.1 |
| 4,610,868 | 9/1986 | Fountain et al. ............. 424/1.1 |
| 4,677,099 | 6/1987 | Shinitzky et al. ............. 514/78 |
| 4,749,585 | 6/1988 | Greco et al. .................. 427/2 |

(List continued on next page.)

FOREIGN PATENT DOCUMENTS

| | | |
|---|---|---|
| 2040914 | 4/1991 | Canada . |
| 0217419 | 4/1987 | European Pat. Off. . |
| 0357581 | 7/1990 | European Pat. Off. . |
| 0416527 | 3/1991 | European Pat. Off. . |
| 0512916 | 11/1992 | European Pat. Off. . |
| 8809170 | 12/1988 | WIPO . |
| 9002545 | 3/1990 | WIPO . |
| WO9300894 | 1/1993 | WIPO . |
| WO9503787 | 2/1995 | WIPO . |
| WO9603991 | 2/1996 | WIPO . |
| WO9616644 | 6/1996 | WIPO . |

OTHER PUBLICATIONS

G. Storm, C. Oussoren, P. Peeters, Y. Barenholz, Tolerability of Liposomes In Vivo, Chapter 22 of *Liposome Technology*, vol. III.
The Washington Post Parade Magazine, Better Sex for Elders, Mar. 16, 1997.
Porst, et al., Intracavernous Self-Injection Therapy with Prostaglandin El-Results of a Multicenter Study with 189 Patients, 1990.
Stackl, et al., Prostaglandin E1-4 Years Experience of Intracavernous Injection, 1990.
Microfluidics Corp., Laboratory Microfluidizer M-110 Series.
SCRIP No 2036, Jun. 23, 1995, Vivus' MUSE for erectile dysfunction.
Crenshaw, Use of Intraurethral Prostaglandin in the Treatment of Impotence.
Balazsovits, et al, Analysis of the Effect of Liposome Encapsulation on the Vesicant Properties, Acute and Cardiac Toxicities, and Antitumor Efficacy of Doxorubicin, 1989.
Cowens, et al, Initial Clinical (Phase I) Trial of TLC D-99 (Doxorubicin Encapsulated in Liposomes), 1993.

*Primary Examiner*—Gollamudi S. Kishore
*Attorney, Agent, or Firm*—Christie, Parker & Hale, LLP

[57] ABSTRACT

A method for the treatment of erectile dysfunction comprises instilling intra meatally an aqueous solution containing prostaglandin-containing liposomes and a detergent for lysing the liposomes. A pharmaceutical composition for treating erectile dysfunction comprises a two-component system. The first component comprises a predetermined amount of lyophilized prostaglandin-containing liposomes. The second component comprises a predetermined volume of an aqueous solution containing a detergent, preferably PEG(9) octylphenyl ether, for lysing the liposomes. Dissolution of the lyophilized prostaglandin-containing liposomes yields a liquid composition suitable for application to the penis, preferably intra meatally, to effect erection.

49 Claims, 1 Drawing Sheet

U.S. PATENT DOCUMENTS

| | | | |
|---|---|---|---|
| 4,776,848 | 10/1988 | Solazzo | 604/247 |
| 4,776,991 | 10/1988 | Farmer et al. | 264/4.3 |
| 4,801,587 | 1/1989 | Voss et al. | 514/248 |
| 4,820,732 | 4/1989 | Shell et al. | 514/573 |
| 4,880,835 | 11/1989 | Janoff et al. | 424/450 |
| 4,955,878 | 9/1990 | See et al. | 604/181 |
| 4,975,282 | 12/1990 | Cullis et al. | 424/450 |
| 5,008,050 | 4/1991 | Cullis et al. | 264/4.3 |
| 5,040,453 | 8/1991 | Lenk et al. | 424/450 |
| 5,082,664 | 1/1992 | Lenk et al. | 424/450 |
| 5,192,806 | 3/1993 | Pill et al. | 514/562 |
| 5,242,391 | 9/1993 | Place et al. | 604/60 |
| 5,256,652 | 10/1993 | El-Rashidy | 514/58 |
| 5,336,678 | 8/1994 | Cavallini | 514/275 |
| 5,370,613 | 12/1994 | Helmy | 604/93 |
| 5,399,581 | 3/1995 | Laragh | 514/396 |
| 5,419,763 | 5/1995 | Hildebrand | 604/54 |
| 5,422,371 | 6/1995 | Liao et al. | 514/560 |
| 5,474,535 | 12/1995 | Place et al. | 604/60 |
| 5,482,039 | 1/1996 | Place | 128/653.1 |
| 5,492,911 | 2/1996 | Stief | 514/252 |

PGE-1 CONTAINING LYOPHILIZED LIPOSOMES FOR USE IN THE TREATMENT OF ERECTILE DYSFUNCTION

FIELD OF THE INVENTION

This invention relates to the treatment of erectile dysfunction, and more particularly to the intra meatal administration of prostaglandin-containing liposomes to effect tumescence and rigidity.

BACKGROUND OF THE INVENTION

The male erectile response is a vascular effect initiated by neuronal action and maintained by a complex interplay between vascular and neurologic effects. Parasympathetic input allows erection by relaxation of trabecular smooth muscle and dilation of the Pilocene arteries of the penis. This leads to extension of the lacunar spaces and entrapment of blood by compressing venules against the tunica albuginea. Erectile dysfunction or impotence is a consistent inability to achieve or sustain an erection of sufficient rigidity for sexual intercourse. The degree of erectile dysfunction varies and they range from a partial decrease in penile rigidity or the inability to sustain an erection to complete erectile failure.

Treatments for erectile dysfunction include vacuum constrictive devices, vascular surgery, penile prostheses, psychosexual therapy, hormonal therapy, and the administration of vasodilators. It has been found that direct injection of vasodilator substances into the corpora of the penis is a highly successful method for producing a rapid onset of erection in many patients. The most effective and well studied agents used in direct injection include papaverine hydrochloride, phentolamine, and alprostadil or prostaglandin E-1 (PGE-1). These have been used either singly or in combination. While generally effective, this procedure is often found to be psychologically disturbing, painful, traumatic or inconvenient as shown by a high rate of patient dropout. Moreover, infection, penile corporal fibrosis, fibrotic nodules, hypotension and priapism may ensue.

Vasodilator substances have also been administered through the urethra. This is described, for example, in U.S. Pat. No. 4,801,578 to Voss, U.S. Pat. No. 4,242,391 to Place, et al., and European Patent Application No. 0,357,581 to Kock.

Papavarine hydrochloride dilates both arterials and venules which results in venous leakage. Phentalomine affects sympathetic innervation which is not always the cause of erective dysfunction, PGE-1 selectively dilates arteriolar and/or nerves thereby inducing vascular engorgement of the corpora cavernosa.

While prostaglandins, particularly prostaglandin E-1, have been shown to be effective in producing erection by direct needle injection into the corpora, the use of prostaglandins in treating erectile dysfunction has been limited due to their short shelf life. Prostaglandins are very unstable and are difficult to produce in a pharmaceutically stable formulation. For example, in aqueous solution, prostaglandin E-1 has a shelf life of only approximately 90 seconds. This means that, to be useful, it must be dissolved and injected or applied immediately. For external or intra meatal applications, nonliposomal prostaglandins are not favored because substantial degradation occurs before enough prostaglandin can diffuse across the epidermis or urethral membrane into the corpora cavernosa to cause erection.

SUMMARY OF THE INVENTION

The present invention provides pharmaceutical compositions and methods for treating erectile dysfunction. Preferred pharmaceutical compositions include a two component system, one component comprising prostaglandin-containing liposomes (also referred to as "liposomal PG") and a second component comprising an aqueous activator solution comprising chemical means for controllably lysing the liposomes to free the prostaglandin contained therein. To increase the shelf life of the product, the liposomal PG are preferably lyophilized. In a preferred embodiment, the prostaglandin is prostaglandin E-1 ("PGE-1"). Preferred means for controllably lysing the liposomes comprises an aqueous solution of a nontoxic detergent, preferably PEG(9) octylphenyl ether. To treat erectile dysfunction, the two components are mixed together to form a solution which is then applied to the penis, either externally or, more preferably, intra meatally, to produce a satisfactory erection.

In the method of the present invention for treating erectile dysfunction, a composition comprising liposomal PG is applied to the penis. Application may be external or, more preferably, intra meatal. If external, the composition may be in the form of an aqueous solution or a cream or ointment. If administered intra meatally, it is preferred that the composition be in the form of an aqueous solution. The amount of prostaglandin administered is preferably from about 0.25 mg to about 5 mg and more preferably from about 1 mg to about 2.5 mg. It is preferred that the solution be administered intra meatally in one or more doses of from about 0.5 cc to about 1 cc.

In a preferred method of the invention, lyophilized liposomal PG is dissolved in an aqueous activator solution containing a detergent, preferably PEG(9) octylphenyl ether. The amount of liposomal PG in the solution is preferably selected to produce a solution containing from about 0.25 mg/cc to about 6 or more mg/cc prostaglandin and preferably from about 0.5 mg/cc to about 2 mg/cc. The concentration of detergent in the solution is preferably from about 0.02% to about 2% and preferably from 0.05% to about 0.25% by weight to thereby effect lysing of the liposome over a period of preferably not more than about 20 minutes and more preferably not more than about 5 to 10 minutes and even more preferably within about 2 to 5 minutes of mixing. After adding the liquid detergent to the lyophilized liposomal PG, the solution is vigorously shaken for 1 to 3 minutes, then the solution is allowed to clear, generally requiring 2 to 5 minutes.

In a preferred method, the liposomal PG solution is administered intra meatally through a soft elongated 10 to 15 mm nipple. With the patient lying on his back, a thin elongated nipple is inserted into the urethra to a distance of about 1 cm to about 2 cm from the meatal opening of the penis and a selected amount of the solution preferably 0.5 to about 1 cc, is instilled through the nipple. The solution is instilled slowly to minimize leakage. Typically, onset of tumescence occurs within 1 to 3 minutes, with full tumescence reached within 5 to 10 minutes lasting 20 to 40 minutes or more. Multiple doses may be instilled, if needed, to produce a satisfactory erection for sexual intercourse.

In an alternate embodiment, the lyophilized liposomal PG and activator solution are mixed in the reservoir of a condom. Once the liposomal PG is dissolved, the condom is fitted over the penis and massaged to spread the liquid over the penis. Satisfactory erections are generally attained within 5 to 10 minutes.

DETAILED DESCRIPTION

Figure 1:
FIG. 1 is a side view of a preferred delivery system.

A particularly preferred pharmaceutical for the treatment of erectile dysfunction comprises a two-component system.

The first component comprises dry lyophilized prostaglandin containing liposomes. The second component comprises an aqueous activator solution containing a liposomal lysing agent, preferably a detergent.

Prostaglandins suitable for use in the present invention include prostaglandin E (PGE), including PGE-1, PGE-2 and PGE-3, prostaglandin A (PGA), including PGA-1, prostaglandin F (PGF), including PGF-2, prostaglandin D (PGD), including PGD-2, prostacylins, thromboxanes, leukotrienes, 6-keto-PGE-1 derivatives, carbacyclin derivatives, PGD-2 derivatives and the like. PGE-1 and PGE-2 are the preferred prostaglandins and PGE-1 is the most preferred prostaglandin.

The liposomes of the present invention may be made of any suitable phospholipid, glycolipid, derived lipid, and the like. Examples of suitable phospholipids include phosphatide choline, phosphatidyl serine, phosphatidic acid, phosphatidyl glycerin, phosphatidyl ethanolamine, phosphatidyl inositol, sphingomyelin, dicetyl phosphate, lysophosphatidyl choline and mixtures thereof, such as soybean phospholipids, and egg yolk phospholipids. Suitable glycolipids include cerebroside, sulphur-containing lipids, ganglioside and the like. Suitable derived lipids include cholic acid, deoxycholic acid, and the like. The presently preferred lipid for forming the liposomes is egg phosphatidylcholine.

The liposomes may be formed by any of the known methods for forming liposomes and may be loaded with prostaglandin according to known procedures. Known methods for forming liposomal PG are described, for example, in PCT Application No. PCT/US88/01714 and European Patent Application No. EP 0,512,916A2, both assigned to the Liposome Company, and European Patent Application No. EP 0,416,527A2 assigned to the Green Cross Corporation, and the references disclosed in those applications, all of which are incorporated herein by reference. What is formed is an emulsion comprising liposomal PG. It is understood that, in addition to prostaglandin, the liposomes may be loaded with other drugs such as papavarine hydrochloride and/or phentolamine.

It is preferred that the liposomes used in the present invention have an average mean diameter from about 20 nm to about 1000 nm and preferably of from about 100 nm to about 200 nm. Art average mean diameter of about 140 nm is particularly preferred. Liposomes larger than about 1000 nm are not preferred because they are difficult to make. Liposomes smaller than about 20 nm are usable but not preferred because they are difficult to make.

Accordingly, the liposomes produced are preferably treated to reduce their size and to produce a homogeneous population. This may be accomplished by conventional techniques such as extrusion through a filter preferably of 100 to 500 nm pour size, the filter being either the straight path or tortuous path type. Other methods of size reducing the liposomes to a homogenous size distribution are ultrasonic exposure, the French press technique, hydrodynamic shearing, homogenization using, for example, a colloid mill or Gaulin homogenizer or microfluidization techniques. Microfluidization is presently preferred.

Microfluidization is described, for example, in U.S. Pat. No. 4,533,254 to Cook, et al., which is incorporated herein by reference. In a preferred microfluidization procedure, the liposomal emulsion is forced at high pressure through a small diameter opening and splattered onto a wall and then collected.

In a particularly preferred embodiment of the invention, the liposomes are passed one to ten and preferably four times through an M-110 Series Laboratory Microfluidizer manufactured by Microfluidics Corporation at a pressure of, e.g., 14000–16000 pounds per square inch to achieve a generally homogenous population of liposomes having an average mean diameter of about 140 nm.

The aqueous emulsion of liposomal PG is stable for days as compared to minutes for prostaglandins. To further stabilize liposomal PG, the emulsion is preferably lyophilized. It has been shown that lyophilized liposomal PG can be stored at room temperature for one half to three years without degradation of the liposomes or prostaglandin.

Lyophilization may be accomplished by any method known in the art. Such procedures are disclosed, for example, in U.S. Pat. No. 4,880,835 to Janoff, et al., which is incorporated herein by reference. Lyophilization procedures preferably include the addition of a drying protectant to the liposome suspension. The drying protectant stabilizes the liposomes so that the size and content are maintained during the drying procedure and through rehydration. Preferred drying agents are saccharide sugars including dextrose, sucrose, maltose, manose, galactose, raffinose, trehalose lactose, and triose sugars which are preferably added in amounts of about 5% to about 20% and preferably about 10% by weight of the aqueous phase of the liposomal suspension. Dextrose, sucrose and maltose are presently preferred. Manitol may be used in conjunction with any of the saccharides. Additional preservatives such as BHT or EDTA, urea, albumin, dextran or polyvinyl alcohol may also be used.

The activator solution comprises a liposome lysing means may be any chemical soluble in water which is capable of lysing the liposomes without degrading the prostaglandin and which is nontoxic and nonirritating in the concentration used to the patient. Preferred lysing means include detergents. Nonlimiting examples of suitable detergents include the sodium salt of cholic acid, dodecyl-β-D-maltosile, lauryldimethylamine oxide, PEG(9) octylphenyl ether (Triton® X-100) and polysorbate 20 (Tween® 20). PEG(9) octylphenyl ether is presently preferred.

The concentration of lysing agent is important. If the lysing agent is too concentrated, the prostaglandin is released too early and is deactivated prior to absorption. If too little is used, an insufficient quantity of prostaglandin is released. Preferably, the concentration of lysing agent is selected to be the minimum amount capable of lysing the liposomes within the desired time after mixing, preferably within 20 minutes, more preferably within 5 to 10 minutes and even more preferably within about 2 to 5 minutes. It is desired to use the minimal effective amount of lysing agent to thereby minimize any potential irritation to the patient. An amount of from about 0.02% to about 2% or more by weight of detergent lysing agent has been found to be effective in lysing the liposomes. A range of from about 0.05% to about 0.25% is presently preferred as providing the best combination of optimal time for lysing the liposomes (2 to 5 minutes), and minimal irritation to the penis.

It is known that about 10 to 20 μg of prostaglandin E-1 needle injected directly into the corpora cavernosa causes a vasodilatory effect resulting in tumescence and rigidity. Accordingly, it is desired to use an amount of liposomal PG that results in at least about 10 to 20 μm of prostaglandin crossing the meatal or urethral membrane into the corpora cavernosa. It has been found that approximately 1% to 5% of a 1 mg dose of prostaglandin E-1 diffuses across the urethral membrane into the corpora cavernosa.

Accordingly, a 1 mg dose of liposomal PGE-1 is presently preferred although higher doses of up to about 6 mg may be used. Doses higher than about 6 mg are not preferred because no additional benefit is seen. Doses as low as about 0.25 mg may also be effective in some individuals.

Due to the limited volume of the urethra, the dose of liposomal PG must be administered in a volume of no more than about 2 cc and preferably of from about 0.5 to 1 cc of solution. Larger amounts are not preferred as there is a greater tendency toward leakage through the meatus. It is understood that multiple doses may be administered if needed.

To determine the amount of liposomal PG necessary to deliver the desired dose of prostaglandin, it was necessary to determine how much prostaglandin is present.

Analysis using a standard prostaglandin E-2 ELISA test established that prostaglandin can be loaded into liposomes in amounts as high as 20% to 40% by weight. However, it is preferred that the prostaglandin be present in the liposomes in an amount of from about 2% to about 3% by weight. A particularly preferred lyophilized liposomal PG composition comprises 44 mg egg phosphotidylcholine, 75 mg maltose and 1 mg prostaglandin E-1.

It is presently preferred that the dissolved liposomal PG solution be administered intra meatally. As used herein "intra meatal" administration refers to and includes administration of the solution in any portion of the ureter within the penis although administration of solution within the portion of the ureter extending through the meatus, i.e., within about 2 to 3 cm from the meatal opening is preferred.

A preferred delivery system for intra meatal administration of the dissolved liposomal PG is shown in FIG. 1 hereto. The delivery system comprises a plastic vial 10 containing the lyophilized liposomal PG and into which the activator solution (generally 1 cc) is introduced. The vial 10 has a screw-on cap (not shown) to seal the vial, which is then shaken vigorously to mix the contents and dissolve the lyophilized liposomal PG. After allowing the product to stand for about 2 to 5 minutes, the cap is removed and a soft plastic or rubber nipple 12 is press fitted into the vial opening. The nipple 12 has a diameter of about 1 mm and a length of about 2 cm.

In accordance with a preferred method of the present invention using the delivery system shown in FIG. 1, the patient is positioned supine on his back. The nipple portion of the vial is then gently inserted into the opening of the urethra and held firmly in place. The vial is then squeezed, pushing a portion of the contents of the vial into the urethra. The expended portion is stroked toward the base of the penis to prevent leakage. This is repeated until the entire contents of the vial has been delivered. The meatal opening is then held shut for a period of, for example, 5 to 10 minutes during which time full tumescence and rigidity is typically reached.

An alternative delivery system comprises a conventional condom. The condom is partially unrolled and the lyophilized liposomal PG is placed in the reservoir of the condom. The aqueous activator solution is then introduced into the reservoir and the contents are mixed until the liposomal PG is dissolved. The condom is then rolled onto the penis which is then massaged to spread the liquid evenly over the penis. Full tumescence is generally reached within 5 to 10 minutes.

It is understood that a wide variety of modifications can be made to the described preferred embodiments of the products and processes without departing from the scope of the present invention. For example, while lyophilization is preferred for increasing shelf life, it is not necessary for the practice of the present invention. Likewise, while the presence of a lysing agent enables controlled release of the prostaglandin, the presence of a lysing agent is not required to practice the claimed method. In such an embodiment, it is preferred that the concentrations of prostaglandin in the liposomes be increased to assume that an adequate amount of prostaglandin is released after administration.

If administered externally, the activator "solution" may comprise a lotion or ointment as described, for example, in U.S. Pat. No. 4,801,587 to Voss, et al., which is incorporated herein by reference.

The efficacy of the present invention is demonstrated by the following examples. As used therein, "level" or "grade" of erection means that amount of tumescence estimated by the patient or the doctor. It is expressed as a ratio, e.g., 2/10, where 10 means full tumescence. "Tumescence" means the amount of vascular engorgement, both elongation and circumferential. It is estimated by the patient or doctor and expressed as a percentage of full or maximum tumescence. "Rigidity" means inability of the penis to buckle. It is estimated by the patient or doctor and expressed as a percentage of rigidity when full tumescence is achieved. "Turgidity" means the amount of circumferential enlargement. It is also estimated by the patient or doctor and is expressed as a percentage of the turgidity achieved at full tumescence.

EXAMPLE 1

Preparation of Lyophilized PGE-1 Liposomes

Liposomal PGE-1 used in the patient studies described in the examples below was prepared according to the following procedure.

1. 2250 ml of water (double distilled) to beaker (Keep Cool) and set with a nitrogen sparge for at least 30 minutes.

2. Add 225 gms of maltose (Sigma M5885) to the water and mix until dissolved. Keep the nitrogen sparge going. Mixture at ph of 4.81.

3. In another beaker 10.59 gms of egg phosphatidylcholine (EPC) (Sigma) is combined with 8.38 ml of ethanol (anhydrous, Sigma E3884) and mixed until dissolved. To this add 67.5 mg of BHT and mix until dissolved. To this mixture add 2160 mg of PGE-1 and mix until dissolved. Use the remaining 4.19 ml of ethanol to rinse any remaining PGE-1 in the weighing container into the mixture.

4. Draw the ethanol solution into a 10 ml glass syringe and add to the maltose solution over 11 minutes with continued nitrogen sparge. Keep ph <7.0 (goes into microfluidizer at ph 4.81). Measure. Hand blade mixture. Keep everything cool 1.5 degrees C.

5. Microfluidizer. Four (4) passes through the microfluidizer 110F:

|  | Total Weight of Materials to be Used* | 9,000 Units Based on Previous Run (886 Units)* |
|---|---|---|
| EPC | 10.59 grams | 107.573 grams |
| Maltose | 225 grams | 2,285.55 grams |
| Ethanol | 12.57 ml | 127.69 ml |
| BHT | 67.5 mg | 685.66 mg |
| PGE-1 | 2160 mg | 21,941 grams |
| (USP) Water | 2250 ml | 22,855.5 ml |

Pressure 16,000 PSI
Caution-keep acidic, keep temp (melting point 115 degrees)
Note-Maltose melting point 102–103 degrees Centigrade
*Multiplier + 10.158

6. Take 2.7 ml of the finished product and lyophilize in approximately 1,000–6 ml Wheaton eye dropper bottles.

Lyophilization was accomplished according to the following cycle:

1. Shelf at ≦−45° C. for at least one (1) hour before loading.

2. Load product keep at ≦−45° C. for twelve (12) hours.

3. Vacuum to ~50 μ.

4. Shelf temperature at −28° C. to −20° C. for 59 hours.

5. Shelf temperature rose from −20° C. to −5° C. during subsequent ten (10) hours. Visually product needed extra time at −20° C.

6. Shelf reset at −22° C. and maintained at −22° C. to −18° C. for thirty-six (36) hours.

7. Shelf reset +25° C. and held at 25° C. for 48 hours.

It is anticipated that the following lyophilization cycle will provide the same results in a shorter time.

1. Shelf to ≦−45° C. for at least one (1) hour before loading.

2. Load product, keep at ≦−45° C. for at least six (6) hours.

3. Vacuum to ≦100 μ.

4. Shelf to −28° C. for 50 hours.

5. Shelf to +25° C. for 40–50 hours.

EXAMPLES 2–13

Patient Studies

The following are examples of the intra meatal administration to male patients suffering erectile dysfunction of compositions comprising PGE-1, PGE-1 containing liposomes in varying concentrations or a placebo.

EXAMPLE 2

Patient History

The patient was a 47-year old white male suffering psychogenic impotence. The patient had no salient medical features, no allergies, no hospitalizations, and currently was taking no medications. Physical examination showed: pulse 70; respiration 16; blood pressure: 140/90; physically within normal limits.

Experimental Procedure

Trial No. 1: 10 cc of a solution containing 0.25% buffered acetate was introduced into a tube containing 2 mg of PGE-1 in the form of a white crystalline powder to achieve a concentration of 0.2 mg/cc. It was noted that there was an odor of vinegar. The white crystalline powder when mixed with the buffer solution did not completely dissolve. The particulate crystalline nature of the mixture did not change appreciatively with either time, mixing by shaking, or with increase of temperature to room temperature (72° F.). One cc of the solution was drawn up into a dropper which was inserted into the urethral meatus of the patient wherein the solution was instilled. The patient noted stinging/burning sensation of the opening. It was not possible to insert the entire volume into the urethra and an immeasurable amount of leakage occurred. No erection occurred. A second dosage using the same volume and milligram dosage of the white crystalline material was administered to the patient, with essentially the same results.

Trial No. 2: A second vial containing 4 mg of PGE-1 was mixed with 2 cc of the same buffer used in Trial No. 1 to achieve a concentration of 2 mg/cc. The crystalline particulate nature of the solution was again noted. One cc of the solution was instilled into the urethral meatus as in Trial No. 1. The patient again noted some slight stinging/burning with discomfort increasing with increase of pressure to the urethra upon filling with the solution. Transient erective activity was noted. The glans penis enlarged to 70% erect size (as recorded by the patient). Patient also noted the feeling of engorgement of the penis. The penile shaft engorged by 50% and elongation occurred of 50%. This transient effect lasted approximately 30 seconds. There was no rigidity of erection, only turgidity.

A second instillation of 1 cc did not provide any response by the patient except for complaint of stinging at the urethral opening and pressure from the instillation.

Phone report by patient after 3 hrs. Patient noted that he had a fullness sensation in the groin and penis, like he has had erection and sex. Patient noted no pain or residue from tests. He indicated that penis still feels engorged as if it were post coital. Only slight stinging sensation in the meatus.

EXAMPLE 3

Patient History

No relevant health history. Physical examination showed Height 5'9"; weight 165; blood pressure 142/98; pulse 88; physically within normal limits.

No prior sexual dysfunction.

Experimental Procedure

PGE-1 was added to 10 cc of a buffer solution containing 0.25% buffered acetate to make a solution of 4 mg of PGE-1 per cc of solution. All material appeared to dissolve in solution. The patient was put in supine position on examination table and ½ (0.5) cc of solution was instilled with an eye dropper into the urethra of the patient. A ring of K-Y jelly was put on the eyedropper 1 cm up the glass from tip so the meatus could be closed and the solution would not back flow or drip out. The patient was treated 4 times within a 30-minute interval, about every 7 minutes. No discomfort. No burning, either in urethra or meatus. No sensation of fullness in urethra or discomfort with insertion of material. Penis was observed over a 1 hour period. After 2 mg, no reaction. After 4 mg, some tumescence. After 6 mg slightly more engorgement. After 8 mg, a grade 2–3/10 erection was achieved but no more after next hour.

Patient contacted after 2 and 3 hour intervals. No further engorgement occurred.

EXAMPLE 4

Patient History

Health History: Cardiac disease (pericarditis) at 34. Hospitalized for 2 weeks. Right knee meniscectomy at 36. No current c.c. No current meds. No history of sexual dysfunction. Physical examination showed NAD within normal limits; blood pressure 130/82; pulse 80; weight 160; height 5'10".

Experimental Procedure

Crystalline liposomal PGE-1 was dissolved in buffer solution containing 2% detergent PEG(9) octylphenyl ether to form 2 mg PGE-1/cc solution. The patient was placed in a supine position and a thin 1½ cm soft nipple was used to instill solution into the urethral meatus in ½ cc increments. The patient was instilled twice over a 10-minute period. The patient complained of slight meatal burning/stinging. Engorgement to the 2–3/10 erection grade level noted after second instillation. Patient subjectively reported some burning. He also noted a feeling of fullness in the groin, and that he felt it would be very easy to "get an erection" with sexual stimulation.

Post check after 2 and 3 hours: Patient reported after leaving that he masturbated to ejaculation to relieve sensation of fullness.

EXAMPLE 5

Patient History

This is the same patient who participated in the experiment procedure described in Example 4.

Experimental Procedure

A vial containing 500 mg lyophilized PGE-1 containing liposomes was diluted with 3 cc of a buffer containing 1% detergent PEG(9) octylphenyl ether to yield a solution containing 1 mg/cc PGE-1. With 5 minutes of vigorous shaking, the entire contents of the vial were dissolved and there was no particulate matter noted. There was no odor to the contents. The patient was placed in a supine position on an examination table and 0.5 cc of the solution was drawn into an eyedropper and administered intra meatally. A ring of K-Y jelly placed 1 cm up the eye dropper kept seepage to a minimum.

After the first instillation, there was no reaction, but the subject complained of burning sensation in the urethra. After 5 minutes a second dose of 0.5 cc was instilled and the patient achieved a 2-3/10 grade erection of transitory nature.

After a lapse of 4 minutes, a third dose of 0.5 cc of the solution was instilled and the subject achieved a 4-5/10 grade erection. After another 5 minutes, a fourth dose of 0.5 cc of the solution was instilled and the erection did not achieve more than a grade 4/10 quality. There was only turgidity and not rigidity. The patient then stood up and the erection increased to a grade 7/10. He was asked to lie back down and the erection decreased to a grade 3/10. After 4 minutes he again stood up and the erection increased to 7/10 once again. The patient elected not to have any more instillations to the urethra at this time. One hour after the experiment the patient reported that the erection was still a grade 3/10. Two hours after the experiment, the patient reported that the erection was still a grade 3/10 and on his first voiding there was a burning sensation. Three hours after the experiment, all signs of engorgement had disappeared.

EXAMPLE 6

Patient History

A 73 year-old male was the subject of this experiment. The patient had the sexual dysfunction of losing erections after approximately 3 minutes after penetration, but had no difficulty with ejaculation. His a.m. erections were grade 10/10, and he had no history of vascular insufficiency. Medical history that was pertinent was that he was taking Hytrin 2QD for blood pressure and Provocol for cholesterol. History was taken and physical examination was given. All within normal limits.

Experimental Procedure

A vial containing lyophilized PGE-1 containing liposomes was mixed with 8 cc of buffer comprising 1% detergent PEG(9) octylphenyl ether to make a solution containing 1 mg/cc PGE-1. One cc increments of the resulting solution were instilled for a total of 3 installations.

There was no response from the first two instillations. On the third installation, the patient obtained an erection of grade 7/10 and was sufficient for penetration. The right corpora cavernosa filled, and the spongiosa filled but the left did not fill, causing the penis to angle left due to a deficiency of left corporal filling. The patient complained of slight stinging after instillation and leakage was kept to a minimum by the previously described use to K-Y jelly.

EXAMPLE 7

Patient History

The patient was a 52 year-old white male. The patient was given a full medical examination and there were no abnormal pathological findings. He has a six-year history of diabetes mellitus for which he takes Diabenase 250 mg B.I.D. The patient does not smoke or drink. There are no other contributory health factors. The patient noted the slow onset of impotence approximately 2 years prior to this evaluation. The patient is in a stable marriage of 20 years duration, and he and his wife attempt intercourse approximately once per week with 25% success rate.

Experimental Procedure

To a vial having a nipple tip as shown in FIG. 1 containing lyophilized liposomal PGE-1 was introduced one cc of a buffer, containing 0.5% detergent PEG(9) octylphenyl ether to make a solution containing 1 mg/cc PGE-1. The patient was put in a supine position on the examination table and a bead of K-Y jelly was placed on the nipple tip of the vial container. The mixture was combined 10 minutes prior to patient instillation. The nipple tip was inserted into the urethral meatus of the patient and the entire contents of the container were instilled slowly. The meatal opening was then held closed to prevent leakage for the next five minutes.

This patient obtained 100% tumescence of the penis with about 50% rigidity. He noted that at no time did his penis get more erect than this on its own. The patient was contacted after two hours and stated that, after he was erect for 1.5 hours, he elected to masturbate. The erection was sufficient and after ejaculation, immediate detumescence followed.

EXAMPLE 8

Patient History

This patient was a 48 year-old white male. The patient was given a full medical examination and there were no abnormal pathological findings. The patient had a six-year history of diabetes mellitus for which he takes N.P.H. 40 µ p.m., Seldane 20 mg, Glucatrol 5 mg a.m. The patient did not smoke or drink. There are no other contributory health factors. The patient noted the slow onset of impotence approximately 2 years prior to the evaluation. The patient indicated a stable marriage of 10 years duration wherein intercourse was attempted approximately once per week with 50% success rate.

Experimental Procedure

To a vial having a nipple tip and containing 500 mg lyophilized liposomal PGE-1 was introduced 1 cc buffer containing 0.1% detergent PEG(9) octylphenyl ether to make a solution containing 1 mg/cc PGE-1. The patient was put in a supine position on the examination table and a bead of K-Y jelly was placed on the nipple tip of the vial. The mixture was combined 10 minutes prior to patient instillation. The nipple tip was inserted into the urethral meatus and the entire contents of the container were instilled slowly. The meatal opening was then held closed to prevent leakage for the next five minutes. After pressure was released approximately 90% of the mixture was expelled.

This patient obtained a 50% tumescence of the penis with about 20% rigidity. The patient noted that at no time did his penis get more erect than this on his own.

EXAMPLE 9

Patient History

The patient was a 67 year-old white male. The patient was given a full medical examination, and there were no abnormal pathological findings. The patient suffers from "hay fever" and takes Seldane D. The patient also has high cholesterol and is treated with Lopid 1 QD. The patient does not smoke or drink. There are no other contributory health factors. The patient was hospitalized once at age 32 for kidney stones. Blood pressure 150/78, SMAC, CBC, UA, WNL. The patient noted the slow onset of impotence approximately 4 years prior to the evaluation. The patient is in a stable marriage of 26 years duration and intercourse is attempted approximately once per week with 50% success rate.

Experimental Procedure

To a vial having a nipple tip and containing 500 mg lyophilized liposomal PGE-1 was introduced 1 cc buffer containing 0.025% detergent PEG(9) octylphenyl ether to make a solution containing 0.5 mg/cc PGE-1. The patient was put in a supine position on the examination table and a bead of K-Y jelly was placed on the nipple tip of the vial. The mixture was combined 10 minutes prior to patient instillation. The nipple tip was inserted into the urethral meatus of the patient and the entire contents of the container were instilled slowly. The meatal opening was then held closed to prevent leakage for the next five minutes.

This patient obtained a 50% tumescence of the penis with 0% rigidity. The patient reports that his erections with masturbation and a.m. erections are occasionally 10/10.

EXAMPLE 10

Patient History

This patient is a 55 year-old white male. The patient was given a full medical examination and there were several pathological findings. In 1982 he had an aortic heart valve replacement and in 1949 he had an appendectomy and tonsillectomy. Physical examination reveals an aortic click. There is no pedal edema and his blood pressure is within the normal limits of 120/80. However, he has been treated with Lanoxin 0.25 mg; Zestril 10 mg; and Mevacor 20 mg. He reports that his blood pressure is 160/110 when he is not under treatment. He also has a large right inguinal hernia for which he reports that he is undergoing surgery next week. The patient does not smoke. He does suffer from high cholesterol which is controlled by Mevacor. He drinks moderately, i.e., one beer per day. He has been hospitalized on several occasions for asthma, pneumonia, and suffered from very severe depression following his aortic heart valve replacement. The patient reports that he is also capable at the present time of achieving grade 8/10 to 9/10 erections with attempts at intercourse but generally these subside to 0/10 with penetration or prior to penetration. Attempts at intercourse are usually once per month. The patient reports masturbatory activity twice a week with 8/10 erections throughout the entire course of masturbation, with a 9/10 erection at ejaculation. He reports that the problem of impotence has existed for four years and his marriage of 29 years appears to be intact. He has three male children who are all in good health. Salient historical features are that his father died from a stroke and his brother has kidney disease. His father also had hypertension prior to the stroke.

Experimental Procedure

A vial having a nipple tip and containing 1 cc of a placebo of 0.25% by weight PEG(9) octylphenyl ether was provided. The patient was put in a supine position on the examination table and a bead of K-Y jelly was placed on the nipple tip of the vial. The nipple tip was inserted into the urethral meatus and the entire contents of the vial were instilled slowly. The meatal opening was then held closed to prevent leakage for the next five minutes. There did, however, during the insertion appear to be leakage of approximately one-half of the contents.

The patient obtained zero degree of tumescence of the penis and zero degree of rigidity. He was then examined 10 minutes and 20 minutes post insertion and was asked to call back in three hours. There was no tumescence noted at any time. The patient had no negative results and reported an absence of any adverse side effects. He did say that he had some slight flushing following the instillation but that this has been a symptom he has suffered with for several years.

EXAMPLE 11

Patient History

This is a 58-year-old white male who presented with a chief complaint of intermittent episodic impotence for approximately seven to ten years. At the present time he is divorced but has a current sexual partner, age 52. He attempts intercourse twice a week and uses a vacuum device supplied by Kaiser to obtain an erection. With genital oral sex he obtains a 7/10 erection. He obtains normal nocturnal erections. His SMAC, CBC, UA are all within normal limits and there appear to be no abnormal physiologic difficulties. At the present time he has no medical history or any salient historical features. He had a vasectomy in 1982, left meniscectomy in 1958, a left hydrocele repair in 1955, and a pilonidal cyst repair. There are no other medical history chief complaints. He was given a full medical examination. There are no other contributory health factors that were noted on physical examination.

Experimental Procedure

To a vial containing 500 mg lyophilized liposomal PGE-1 was introduced one cc buffer comprising 1 mg/cc PGE-1. The patient was put in a supine position on the examination table and a bead of K-Y jelly was placed on an eyedropper. The mixture was combined ten minutes prior to patient instillation. The mixture was then drawn into the eyedropper and the eyedropper was inserted into the urethra to a distance of approximately 2.5 cm. The eyedropper was inserted into the urethral meatus and the entire contents were instilled slowly. The meatal opening was then held closed to prevent leakage for the next five minutes.

The patient obtained approximately 80 to 90 percent tumescence with 50 to 60 percent rigidity. He reported back within two hours and reported a "fullness" type of feeling in the groin. He masturbated to relieve this pelvic congestion and noted that the erection subsided within the next 30 minutes, but held at about the 80 percent level during the next two hours, which the patient, noted was sufficient for penetration had an available partner been present.

EXAMPLE 12

Patient History

This patient is a 68-year-old male who presented with a chief complaint of intermittent episodic impotence for approximately ten years. The patient was given a full medical examination and there were no abnormal pathological findings. His father died at age 87 of a stroke. His mother died at age 93 of hypertension. There is no familial history for any other diseases. He has a 56-year-old sister who is in good health. The patient presently takes Hytrin for his prostatic hypertrophy. He has no other medical difficulties. He does not smoke. He drinks 4 ounces of alcohol per week and two cups of coffee per day. The patient is not married and has not been married for the last 15 years; however, he does have multiple female partners. The patient obtains a 10/10 grade a.m. erection and a 10/10 p.m. erection. The patient has not had nocturnal penile tumescence monitoring but his last SMAC, CBC and urinalysis were within normal limits and his last electrocardiogram was within normal limits.

The patient has been using papaverine and Regitine for approximately four years on a two to three time per week basis and has been using papaverine, Regitine and prostaglandin injections for approximately one year. The patient travels to Brazil on an infrequent basis where he uses this daily. He has not suffered from priapism.

Experimental Procedure

To a vial containing 500 mg lyophilized liposomal PGE-1, was introduced 1 cc buffer comprising 0.25% detergent PEG(9) octylphenyl ether making a solution comprising 1 mg/cc PGE-1. The patient was put in a supine position on the examination table and a bead of K-Y jelly was placed on the eyedropper tip to contain the mixture in the urethra. The mixture was then instilled into the urethra approximately 10 minutes after mixture. The meatal opening was then held closed to prevent further leakage for the next 5 minutes.

After the patient sat upright, approximately one-half of the mixture leaked from the urethra. However, the patient went on to obtain 80 percent tumescence with 50 percent rigidity. Ten minutes after this was noted, the patient had a 100 percent erection with full rigidity and full tumescence.

EXAMPLE 13

Patient History

This patient is a 53-year-old white male. The patient was given a full medical examination and there were no abnormal physiologic findings. At the time of examination, he suffered from hemorrhoids, frequent headaches described as nonmigrainous but as tension and back pain for which he has a long history of lower back pain. He also had a disc removal in 1984 of the C7 disc space. He has frequent rashes. Childhood diseases include chickenpox, measles and mumps. He currently drinks one to four drinks per day and smokes about one-half pack of cigarettes per day. Blood pressure was 130/82.

Experimental Procedure

A vial containing 1 cc of a placebo of 0.25% by weight PEG(9) octylphenyl ether was provided. The patient was put in a supine position on an examination table and a very small diameter urethra was noted which barely accommodated the tip of the eye dropper vial. Instillation of the solution was begun, but the patient immediately complained of pain in the meatus and the procedure was stopped for approximately two minutes. The instillation was thereafter continued and approximately half a dropper full of solution was instilled into the urethra before this patient again complained of pain and the procedure was stopped for approximately five minutes. Instillation was resumed and one more dropper full was instilled, but there was massive leakage of the first dropper out of the urethra. The patient did not wish to proceed further with the test at this time since he was experiencing discomfort. There was no erection noted and the meatus was held shut for five minutes to keep solution contained in the urethra intact.

The patient received no erection at time of instillation of the solution and at 20 minutes post experiment the penis was essentially as it was prior to the experiment. There was never any feeling of fullness on the patient's part or any subjective feeling of erection.

The results of Examples 2–13 are tabulated below in Table 1

TABLE 1

| Example | Dose of PGE-1 (nonliposomal) | Dose of PGE-1 (Liposomal) | Conc. of Detergent | Summary of Results |
|---|---|---|---|---|
| 2 (Trial #2) | 0.2 mg | — | — | Transient effect: 70% erection; 50% engorgement; 50% elongation; duration 30 sec. |
| 3 | 2 mg × 2 = 4 mg | — | — | Grade 2–3/10 erection |
| 4 | — | 1 mg × 2 = 2 mg | 2% | Grade 2–3/10 erection |
| 5 | — | 0.5 mg × 4 = 2 mg | 1% | Grade 4–5/10 erection supine; grade 7/10 erection standing; grade 3/10 after 2 hours. |
| 6 | — | 1 mg × 3 = 3 mg | 0.5 | Grade 7/10 erection. |
| 7 | — | 1 mg | 0.25 | 100% tumescence; 50% rigidity; erect for 1.5 hrs. |
| 8 | — | 1 mg | 0.1 | 50% tumescence; 20% rigidity. |
| 9 | — | 0.5 mg | 0.025 | 50% tumescence; 0% rigidity. |
| 10 | — | — | — | 0% tumescence; 0% rigidity. |
| 11 | — | 1 mg | 0.25 | 90% tumescence; 50–60% rigidity, 30 min. full erection; 2 hr. 80% erection. |
| 12 | — | 1 mg | 0.25 | 80% tumescence; 50% rigidity. |
| 13 | 0 | 0 | — | 0% tumescence; 0% rigidity. |

What is claimed is:

1. A method for treating a male patient suffering erectile dysfunction comprising:
   providing a predetermined amount of lyophilized prostaglandin-containing liposomes;
   dissolving the lyophilized prostaglandin-containing liposomes in an aqueous solution;
   contacting the dissolved prostaglandin-containing liposomes with a liposome lysing agent whereby the liposome lysing agent lyses the prostaglandin-containing liposomes over a select period of time to thereby form an active aqueous solution containing released prostaglandin; and
   during the period that the released prostaglandin is active, applying an effective amount of the active aqueous solution containing released prostaglandin to the penis of the patient for a time sufficient to produce erection of the penis.

2. A method as claimed in claim 1 wherein the prostaglandin-containing liposomes contain prostaglandin E-1.

3. A method as claimed in claim 1 wherein the aqueous solution in which the lyophilized prostaglandin-containing solution is dissolved comprises the liposome lysing agent.

4. A method as claimed in claim 1 wherein the active aqueous solution containing released prostaglandin is applied to the penis of the patient intra-meatally.

5. A method as claimed in claim 4 wherein the active aqueous solution containing released prostaglandin is applied in a volume of from about 0.5 cc to about 1 cc.

6. A method as claimed in claim 1 wherein the amount of prostaglandin in the active aqueous solution containing released prostaglandin applied to the penis is up to about 6 mg/cc.

7. A method as claimed in claim 1 wherein the amount of prostaglandin in the active aqueous solution containing released prostaglandins applied to the penis is from about 0.5 mg to about 2.5 mg.

8. A method as claimed in claim 1 wherein the liposomes have a mean average diameter of from about 20 nm to about 1000 nm.

9. A method for treating a male patient suffering erectile dysfunction comprising:
   providing a predetermined amount of lyophilized liposomal PG;
   mixing the lyophilized liposomal PG with a predetermined volume of aqueous activator solution comprising a liposome lysing agent for time sufficient to dissolve the lyophilized liposomal PG and for the liposome lysing agent to lyse at least a portion of the liposomal PG to thereby release PG into the aqueous solution to form an active aqueous mixture; and
   applying an effective amount of the mixture to the penis of the patient for a time sufficient to produce erection of the penis.

10. A method as claimed in claim 9 wherein the predetermined amount of lyophilized liposomal PG and predetermined volume of activator solution are selected to achieve an amount of prostaglandin in the mixture applied to the penis up to about 6 mg.

11. A method as claimed in claim 9 wherein the predetermined amount of lyophilized liposomal PG and predetermined volume of activator solution are selected to achieve an amount of prostaglandin in the mixture applied to the penis of from about 0.05 mg to about 2.5 mg.

12. A method as claimed in claim 9 wherein the liposome lysing agent is a detergent.

13. A method as claimed in claim 12 wherein the detergent is selected from the group consisting of the sodium salt of cholic acid, dodecyl-β-D-maltosile, lauryldimethylamine oxide, PEG(9) octylphenyl ether, polysorbate 20 and mixtures thereof.

14. A method as claimed in claim 12 wherein the detergent is PEG(9) octylphenyl ether.

15. A method as claimed in claim 12 wherein the detergent is present in an amount of from about 0.02% to about 2% by weight.

16. A method as claimed in claim 12 wherein the detergent is present in an amount of from about 0.05% to about 0.25% by weight.

17. A method as claimed in claim 9 wherein the lysing agent lyses substantially all of the liposomal PG within about 20 minutes after dissolution of the lyophilized liposomes in the aqueous activator solution.

18. A method as claimed in claim 9 wherein the lysing agent lyses substantially all of the liposomal PG within about 5 to about 10 minutes after dissolution of the lyophilized liposomes in the aqueous activator solution.

19. A method as claimed in claim 9 wherein the lysing agent lyses substantially all of the liposomal PG within from about 2 to about 5 minutes after the dissolution of the lyophilized liposomes in the aqueous activator solution.

20. A method as claimed in claim 9 wherein the liposomes of the liposomal PG have an average mean diameter of from about 20 nm to about 1000 nm.

21. A method as claimed in claim 9 wherein the liposomes of the liposomal PG have an average mean diameter of from about 100 nm to about 200 nm.

22. A method as claimed in claim 9 wherein the predetermined volume of aqueous activator solution is from about 0.5 cc to about 1 cc and the predetermined amount of lyophilized liposomal PG is selected to achieve a concentration of prostaglandin in the solution of from about 0.5 mg/cc to about 2.5 mg/cc when substantially all of the liposomal PG have been lysed.

23. A method as claimed in claim 9 wherein the liposomal PG comprises prostaglandin E-1.

24. A pharmaceutical kit for use in the treatment of male erectile dysfunction comprising:
   a first component comprising a predetermined amount of liposomal PG;
   a second component different from the first component comprising a predetermined volume of aqueous solution containing a liposomal lysing agent for lysing liposomal PG to release prostaglandin;
   whereby mixture of the first and second components results in a liquid composition containing released prostaglandin which can be applied to the penis to effect erection of the penis.

25. A pharmaceutical kit as claimed in claim 24 wherein the liposomal PG comprises prostaglandin E-1.

26. A pharmaceutical kit as claimed in claim 24 wherein the predetermined amount of liposomal PG and predetermined volume of aqueous solution are selected to achieve a concentration of PC in the liquid composition of from about 0.25 mg/cc to about 6 mg/cc when substantially all of the prostaglandin has been released from the liposomal PG.

27. A pharmaceutical kit as claimed in claim 24 wherein the predetermined amount of liposomal PG and predetermined volume of aqueous solution are selected to achieve a concentration of PG in the liquid composition of from about 0.5 mg/cc to about 2.5 mg/cc when substantially all of the prostaglandin has been released from the liposomal PG.

28. A pharmaceutical kit as claimed in claim 24 wherein the liposomal PG is lyophilized.

29. A pharmaceutical kit as claimed in claim 24 wherein the liposomes of the liposomal PG have a mean average diameter of from about 20 nm to about 1000 nm.

30. A pharmaceutical kit as claimed in claim 24 wherein the liposomes of the liposomal PG have a mean average diameter of from about 100 nm to about 200 nm.

31. A pharmaceutical kit as claimed in claim 24 wherein the liposomal lysing agent is a detergent.

32. A pharmaceutical kit as claimed in claim 24 wherein the liposomal lysing agent is a detergent selected from the group consisting of the sodium salt of cholic acid, dodecyl-β-D-maltosile, lauryldimethylamine oxide, PEG(9) octylphenyl ether, polysorbate 20 and mixtures thereof.

33. A pharmaceutical kit as claimed in claim 24 wherein the liposomal lysing agent is PEG(9) octylphenyl ether.

34. A pharmaceutical kit as claimed in claim 31 wherein the detergent is present in the second component in an amount of from about 0.02% to about 2% by weight.

35. A pharmaceutical kit as claimed in claim 31 wherein the detergent is present in the second component in an amount of from about 0.05% to about 0.25% by weight.

36. A pharmaceutical kit for use in the treatment of male erectile dysfunction comprising:
   a first component comprising a predetermined amount of lyophilized liposomal PG comprising prostaglandin E-1;
   a second component different from the first component comprising a predetermined volume of aqueous solution containing a liposomal lysing agent for lysing liposomal PG to release prostaglandin;

whereby mixture of the first and second components results in a liquid composition containing released prostaglandin which can be applied to the penis to effect erection of the penis.

37. A pharmaceutical kit as claimed in claim 35 wherein the predetermined amount of lyophilized liposomal PG and predetermined volume of aqueous solution are selected to achieve a concentration of PG in the liquid composition of from about 0.25 mg/cc to about 6 mg/cc when substantially all of the prostaglandin has been released from the liposomal PG.

38. A pharmaceutical kit as claimed in claim 35 wherein the predetermined amount of lyophilized liposomal PG and predetermined volume of aqueous solution are selected to achieve a concentration of PG in the liquid composition of from about 0.5 mg/cc to about 2.5 mg/cc when substantially all of the prostaglandin has been released from the liposomal PG.

39. A pharmaceutical kit as claimed in claim 35 wherein the liposomes of the liposomal PG have a size which provides, after reconstitution, a mean average diameter of from about 20 nm to about 1000 nm.

40. A pharmaceutical kit as claimed in claim 35 wherein the liposomes of the liposomal PG have a size which provides, after reconstitution, a mean average diameter of from about 100 nm to about 200 nm.

41. A pharmaceutical kit as claimed in claim 35 wherein the liposomal lysing agent is a detergent.

42. A pharmaceutical kit as claimed in claim 35 wherein the liposomal lysing agent is a detergent selected from the group consisting of the sodium salt of cholic acid, dodecyl-$\beta$-D-maltosile, lauryldimethylamine oxide, PEG(9) octylphenyl ether, polysorbate 20 and mixtures thereof.

43. A pharmaceutical kit as claimed in claim 35 wherein the liposomal lysing agent is PEG(9) octylphenyl ether.

44. A pharmaceutical kit as claimed in claim 41 wherein the detergent is present in the second component in an amount of from about 0.02% to about 2% by weight.

45. A pharmaceutical kit as claimed in claim 41 wherein the detergent is present in the second component in an amount of from about 0.05% to about 0.25% by weight.

46. A method as claimed in claim 1 wherein the liposome lysing agent is a detergent.

47. A method as claimed in claim 45 wherein the detergent is selected from the group consisting of the sodium salt of choleic acid, dodecyl-$\beta$-D-maltosile, lauryldimethylamine oxide, PEG(9) octylphenyl ether, polysorbate 20 and mixtures thereof.

48. A method as claimed in claim 45 wherein the detergent is PEG (9) octylphenyl ether.

49. A method for treating a male patient suffering erectile dysfunction comprising:

providing an aqueous solution comprising prostaglandin-containing liposomes;

lysing the prostaglandin-containing liposomes over a select period of time to thereby form an active aqueous solution containing released prostaglandin; and during the period that the released prostaglandin is active, applying an effective amount of the active aqueous solution containing released prostaglandin to the penis of the patient for a time sufficient to produce erection of the penis.

* * * * *

UNITED STATES PATENT AND TRADEMARK OFFICE
CERTIFICATE OF CORRECTION

PATENT NO. : 5,718,917
DATED : February 17, 1998
INVENTOR(S) : Jackie R. See

It is certified that error appears in the above-indentified patent and that said Letters Patent is hereby corrected as shown below:

Item [56] References Cited, U.S. Patent Documents, page 2, column 1,
      Replace "4,880,835  11/1989  Janoff et al...424/450"
      with  -- 4,880,635  11/1989  Janoff et al...424/450 --.

Insert -- 4,880,835  11/1989  Park..............514/570 --.

Replace "5,040,453  8/1991  Lenk et al......424/450"
      with  -- 5,030,453  7/1991  Lenk et al......424/450 --

Column 2, line 62, change "DRAWINGS" to -- DRAWING --.
Column 3, line 44, change "Art average" to -- An average --.
Column 4, line 14, change "4,880,835" to -- 4,880,635 --.
Column 9, line 56, change "installation" to -- instillation --.
Column 9, line 62, change "use to" to -- use of --.
Column 12, line 10, after "presented" delete "with".
Column 12, line 50, after "presented" delete "with".
Column 17, line 5, change "claim 35" to -- claim 36 --.
Column 17, line 12, change "claim 35" to -- claim 36 --.
Column 17, line 19, change "claim 35" to -- claim 36 --.
Column 17, line 23, change "claim 35" to -- claim 36 --.
Column 17, line 27, change "claim 35" to -- claim 36 --.
Column 17, line 29, change "claim 35" to -- claim 36 --.

UNITED STATES PATENT AND TRADEMARK OFFICE
CERTIFICATE OF CORRECTION

PATENT NO. : 5,718,917
DATED : February 17, 1998
INVENTOR(S) : Jackie R. See

It is certified that error appears in the above-indentified patent and that said Letters Patent is hereby corrected as shown below:

Column 18, line 1, change "claim 35" to -- claim 36 --.
Column 18, line 11, change "claim 45" to -- claim 46 --.
Column 18, line 13, change "choleic" to -- cholic --.
Column 18, line 16, change "claim 45" to -- claim 46 --.

Signed and Sealed this

Twenty-third Day of February, 1999

Attest:

Q. TODD DICKINSON

Attesting Officer     Acting Commissioner of Patents and Trademarks